United States Patent [19]

Jansons et al.

[11] Patent Number: 4,721,771

[45] Date of Patent: * Jan. 26, 1988

[54] PREPARATION OF AROMATIC POLYMERS

[75] Inventors: Viktors Jansons, Los Gatos; Heinrich C. Gors, Mountain View, both of Calif.

[73] Assignee: Raychem Corporation, Menlo Park, Calif.

[*] Notice: The portion of the term of this patent subsequent to Nov. 24, 2004 has been disclaimed.

[21] Appl. No.: 790,030

[22] Filed: Oct. 22, 1985

Related U.S. Application Data

[63] Continuation-in-part of Ser. No. 772,182, Aug. 30, 1985, abandoned, which is a continuation of Ser. No. 659,741, Oct. 11, 1984, abandoned, which is a continuation-in-part of Ser. No. 594,503, Mar. 29, 1984, abandoned, which is a continuation-in-part of Ser. No. 481,083, Mar. 31, 1983, abandoned.

[51] Int. Cl.$^4$ .................... C08G 2/00; C08G 4/00
[52] U.S. Cl. .................... 528/222; 528/223; 528/224; 528/225; 525/242; 525/280; 525/309
[58] Field of Search .............. 528/222, 223, 224, 225; 525/242, 280, 309

[56] References Cited

U.S. PATENT DOCUMENTS

| | | | |
|---|---|---|---|
| 3,065,205 | 11/1962 | Bonner | 528/180 |
| 3,385,825 | 5/1968 | Goodman et al. | 528/176 |
| 3,441,538 | 4/1969 | Marks | 528/86 |
| 3,442,857 | 5/1969 | Thornton | 528/86 |
| 3,516,966 | 6/1970 | Berr | 528/194 |
| 3,524,833 | 8/1970 | Darms | 528/176 |
| 3,767,620 | 11/1971 | Angelo et al. | 525/419 |
| 3,791,890 | 2/1974 | Gander | 528/180 |
| 3,953,400 | 4/1976 | Dahl | 528/125 |
| 3,956,240 | 5/1976 | Dahl et al. | 528/125 |
| 4,008,203 | 2/1977 | Jones | 528/180 |
| 4,052,365 | 10/1977 | Jones | 528/86 |
| 4,229,564 | 10/1980 | Dahl | 528/125 |
| 4,247,682 | 1/1981 | Dahl | 528/125 |
| 4,356,292 | 10/1982 | Sankaran et al. | 528/86 |
| 4,356,298 | 10/1982 | Marvel et al. | 528/176 |
| 4,361,693 | 11/1982 | Jansons | 528/180 |
| 4,396,755 | 8/1983 | Rose | 528/125 |
| 4,398,020 | 8/1983 | Rose | 528/125 |

FOREIGN PATENT DOCUMENTS

| | | |
|---|---|---|
| 4518311 | 10/1965 | Japan . |
| 971227 | 9/1964 | United Kingdom . |
| 1019226 | 2/1966 | United Kingdom . |
| 1086021 | 10/1967 | United Kingdom . |
| 1250251 | 10/1971 | United Kingdom . |
| 1340709 | 12/1973 | United Kingdom . |
| 1383393 | 12/1975 | United Kingdom . |
| 1558615 | 1/1980 | United Kingdom . |

*Primary Examiner*—Morton Foelak
*Assistant Examiner*—M. L. Moore
*Attorney, Agent, or Firm*—Yuan Chao; Edith A. Rice; Herbert G. Burkard

[57] ABSTRACT

Aromatic oligomers, in particular arylene ketone and arylene sulfone oligomers, are prepared by reacting an appropriate monomer system in the presence of free Lewis acid and a complex between a Lewis acid, for example, aluminum trichloride, and a Lewis base, for example, N,N-dimethylformamide, and, optionally, a diluent, such as methylene chloride. The process is particularly advantageous for the preparation of substantially or all paralinked arylene ether ketone oligomers as the presence of the Lewis acid/Lewis base complex markedly reduces alkylation and ensures the substantial absence of ortho substitution. The monomer system can be, for example, a self-reacting monomer such as p-phenoxy-benzoyl chloride or a two-monomer system such as 1,4-diphenoxybenzene and terephthaloyl chloride.

23 Claims, No Drawings

PREPARATION OF AROMATIC POLYMERS

This application is a continuation-in-part of application Ser. No. 772,182, filed Aug. 30, 1985, now abandoned, which is a continuation of application Ser. No. 659,741, filed Oct. 11, 1984, now abandoned, which is a continuation-in-part of application Ser. No. 594,503, filed Mar. 29, 1984, now abandoned, which is a continuation-in-part of application Ser. No. 481,083, filed Mar. 31, 1983, now abandoned, the disclosures of which are incorporated herein by reference.

BACKGROUND OF THE INVENTION

This invention relates to a method of preparing aromatic oligomers such as arylene ketone oligomers and arylene sulfone oligomers, and in particular to an electrophilic reaction process for preparing such oligomers in the presence of a Lewis acid and a complex between a Lewis acid component and a Lewis base component and, optionally, a diluent.

Arylene ketone and arylene sulfone oligomers can be prepared by either one of two approaches: (1) electrophilic synthesis in which an aryl ketone or aryl sulfone linkage is formed or (2) nucleophilic synthesis in which an aryl ether linkage is formed. In an electrophilic synthesis, the reaction involves the formation of an aryl ketone group or aryl sulfone group from a carboxylic acid derivative or sulfonic acid derivative, respectively, and an aromatic compound containing an aromatic carbon bearing an activated hydrogen atom, i.e. a hydrogen atom displaceable under the electrophilic reaction conditions. The monomer system employed in the reaction can be, for example, (a) a single aromatic compound containing a carboxylic acid derivative or sulfonic acid derivative as well as an aromatic carbon bearing a hydrogen atom activated toward electrophilic substitution; or (b) a two-monomer system of a dicarboxylic acid derivative or a disulfonic acid derivative and an aromatic compound containing two such activated hydrogen atoms. An example of a single monomer system is p-phenoxybenzoyl chloride. An appropriate two-monomer system comprises 1,4-diphenoxybenzene and terephthaloyl chloride. Combinations of several such monomers can be used.

Electrophilic reactions of this type are often referred to as Friedel-Crafts reaction. A commonly used medium for such Friedel-Crafts reactions consists of the reactant(s), a catalyst, such as anhydrous aluminum trichloride, and an inert solvent such as methylene chloride. Because carbonyl groups complex with aluminum trichloride and thereby deactivate it, the aluminum trichloride catalyst is generally employed in the preparation of arylene ketones in an amount slightly more than one equivalent for each equivalent of carbonyl groups in the reaction medium. The slight excess assures that enough free aluminum chloride will be present to fulfill its catalytic role. In the preparation of arylene sulfones similar amounts of aluminum trichloride are required for each sulfone group under the preferred reaction conditions. Other metal halides such as ferric chloride may be employed as the catalyst.

SUMMARY OF THE INVENTION

This invention provides a method of preparing an aromatic oligomer having an inherent viscosity of less than about 0.6 and having at least 2 repeat units, which comprises reacting an appropriate arylene carboxylic acid derivative or arylene sulfonic acid derivative in a reaction medium comprising free Lewis acid and a complex between at least one Lewis acid and at least one Lewis base.

More specifically, this invention comprises a method for the preparation of an arylene ketone oligomer by reacting in the presence of free Lewis acid and a complex between a Lewis acid and a Lewis base, a monomer system selected from the group consisting of (a) at least one self oligomerizing monomer of the formula

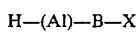

wherein A1 is a divalent aromatic moiety, H is a hydrogen atom displaceable under Friedel-Crafts acylation conditions,

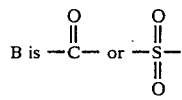

and X is halogen or other leaving group displaceable under Friedel-Crafts acylation conditions; and (b) a monomer system comprising the combination of at least one activated monomer of the formula

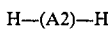

and, in an amount approximately equimolar with said activated monomer, at least one monomer of the formula

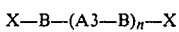

wherein A2 and A3 are divalent aromatic moieties which can be the same or different, B, H and X are as defined above and n is 0–2.

DETAILED DESCRIPTION OF THE INVENTION

Arylene ketone and arylene sulfone oligomers, in particular arylene ether ketone oligomers are useful inter alia as so-called hard blocks in the preparation of di-, tri- or multi-segment block copolymers. When the number of segments is relatively small the hard blocks may contain as many as 100 repeat units, whilst for multi-segmented block copolymers the hard blocks may contain from 10–30 repeat units. They are also useful in the preparation of flame retardants, antioxidants and ultraviolet light stabilizers.

In the electrophilic oligomerization of this invention an arylene ketone or arylene sulfone oligomer is produced from an appropriate monomer system. The oligomers produced by the process of the invention have repeat units of the general formula

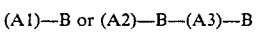

wherein A1, A2, A3 and B are as defined herein. The monomer system can comprise one or more suitable monomers, as defined more fully below.

"Arylene ketone" oligomers contain arylene and ketone groups and may also contain additional groups in the oligomer chain, including, for example, ether, sulfone, sulfide, amide, imide, azo, alkylene, perfluoroalkylene and other appropriate groups. Similarly, "arylene sulfone" oligomers contain arylene and sulfone groups in the oligomer optionally with other linkages. Generally, the monomer system comprises: (a) an aromatic compound containing a carboxylic or sulfonic acid derivative and an aromatic hydrogen atom displaceable under Friedel-Crafts conditions, the hydrogen atom being activated toward electrophilic displacement by, for example, an electron donating group situated ortho or para with respect to said hydrogen atom; or (b) a two-monomer system of a dicarboxylic or disulfonic acid derivative group and an aromatic compound containing two such displaceable hydrogen atoms. The term "aromatic hydrogen atom" refers to a hydrogen atom bound to an aromatic carbon atom, i.e. a carbon atom that is a member of an aromatic ring.

Combinations of different monomers of the same functionally can be co-oligomerized with combinations of different monomers of the complementary functionality, provided the stoichiometric balance necessary to yield oligomers is maintained. Thus, two or more different diacid compounds may be co-oligomerized with one activated-hydrogen compound, or two or more different diacid halides with two or more different activated-hydrogen compounds, etc.

More specifically the monomer or monomers employed are selected from the group consisting of:
(a) at least one self oligomerizing monomer of the formula

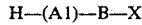

wherein A1 is a divalent aromatic moiety, H is hydrogen displaceable under Friedel-Crafts acylation conditions and B is

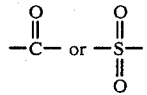

and X is a halogen or other leaving group displaceable under Friedel-Crafts acylation conditions and
(b) a monomer system comprising the combination of at least one activated monomer of the formula

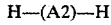

and, in an amount approximately equimolar with said activated monomer, at least one monomer of the formula

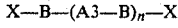

wherein A2 and A3 are divalent aromatic moieties which can be the same or different, B, H and X are as defined above and n is 0-2.

In the above definitions, the term "displaceable under Friedel-Crafts acylation conditions" means that the particular group or atom is displaced from the molecule, i.e. leaves the molecule, under the well known conditions for Friedel-Crafts acylation to occur. In particular, the group or atom is displaceable from the molecule under the reaction conditions of this invention. Such groups are referred to herein in general terms as "leaving groups". The activated hydrogen atoms of the compounds

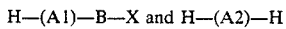

and the groups designated "X" of the compounds

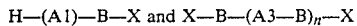

are displaceable under the reaction conditions specified herein. Examples of leaving groups displaceable under Friedel-Crafts acylation conditions include halide, N-imidazolyl, N-pyrazolyl, N-succinimido, N-pyridinium chloride, trimethyl-ammonium chloride, activated alkyl or aryl mercaptides and the like.

The difunctional aromatic moieties A1, A2 and A3, which may be the same or different, include mononuclear moieties, such as phenylene, polynuclear moieties such as biphenylene, heteronuclear moieties such as pyridinediyl or condensed nuclear moieties such as divalent anthrylene. Also included are combinations of such aromatic moieties linked, for example, by nonaromatic groups such as ether, carbonyl, sulfone, alkyl, cycloalkyl, amide sulfide or imide. The aromatic moieties may include pendant substituents such as lower alkyl, halogen, nitro, benzoyl groups or any other atom or group which will not interfere with the reaction. It is to be understood that A1, A2 and A3 moieties present in the monomers used in the reaction should be selected so that they will not interfere with the reaction, for example, by inhibiting or preventing the oligomerization steps or by reacting so as to form crosslinks or branches in the oligomer when such crosslinking or branching is undesired. Further, a hydrogen atom displaceable under Friedel-Crafts acylation conditions is bound to the aromatic moieties A1 and A2. In order that the hydrogen atom be displaceable, such moieties contain activating substituents, such as, for example, electron donating groups.

Preferred divalent aromatic moieties which can be used are of the formula:

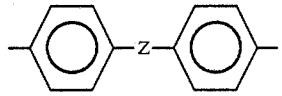

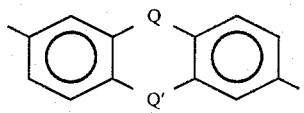

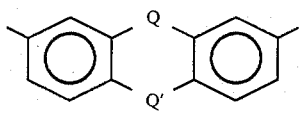

wherein Q' and Q" are independently selected from the group consisting of a direct linkage, —CH2—, —O— and —S—; and Z is, for example, a direct linkage,

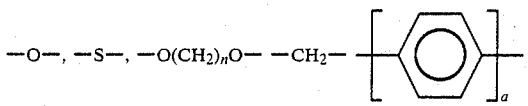

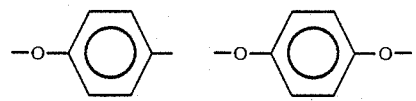

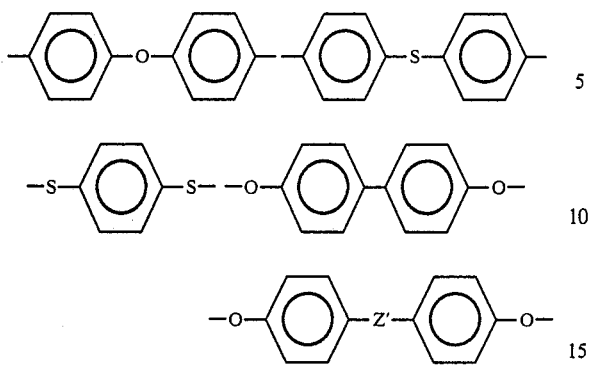

wherein a is 0-4 and Z is, for example, a direct linkage or a divalent radical of the formula

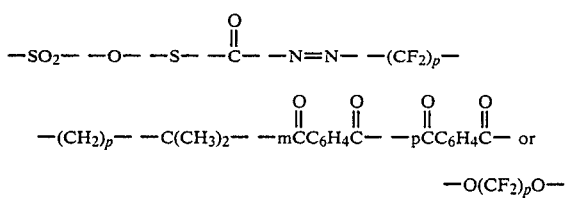

wherein p is 1-20.

Preferred monomers of the formula

H—(A1)—B—X include carboxylic and sulfonic acids in the form of their acid halides or other suitable derivatives. For example, suitable carboxylic acid derivatives are compounds of the formula

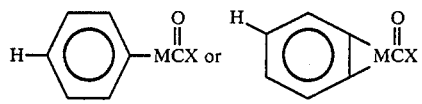

wherein X is halogen or other suitable leaving group and wherein M is an aromatic moiety such that (a) —COX is bonded to M through an aromatic carbon, (b) M is itself unreactive under Friedel-Craft acylation conditions of this invention, and (c) —M—COX experts an electron donating effect on the phenyl group equivalent to a sigma value of −0.10 or less (i.e., more negative) and thereby activating the para positioned aromatic hydrogen, H. A discussion on sigma values may be found in Gordon and Ford, "The Chemist's Companion: A Handbook of Practical Data, Techniques, and References", John Wiley & Sons, 1972, page 144.

Typical carboxylic acid derivatives of this type which can be employed as a monomer in the oligomerization process of this invention include compounds of the following formulas:

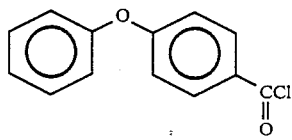

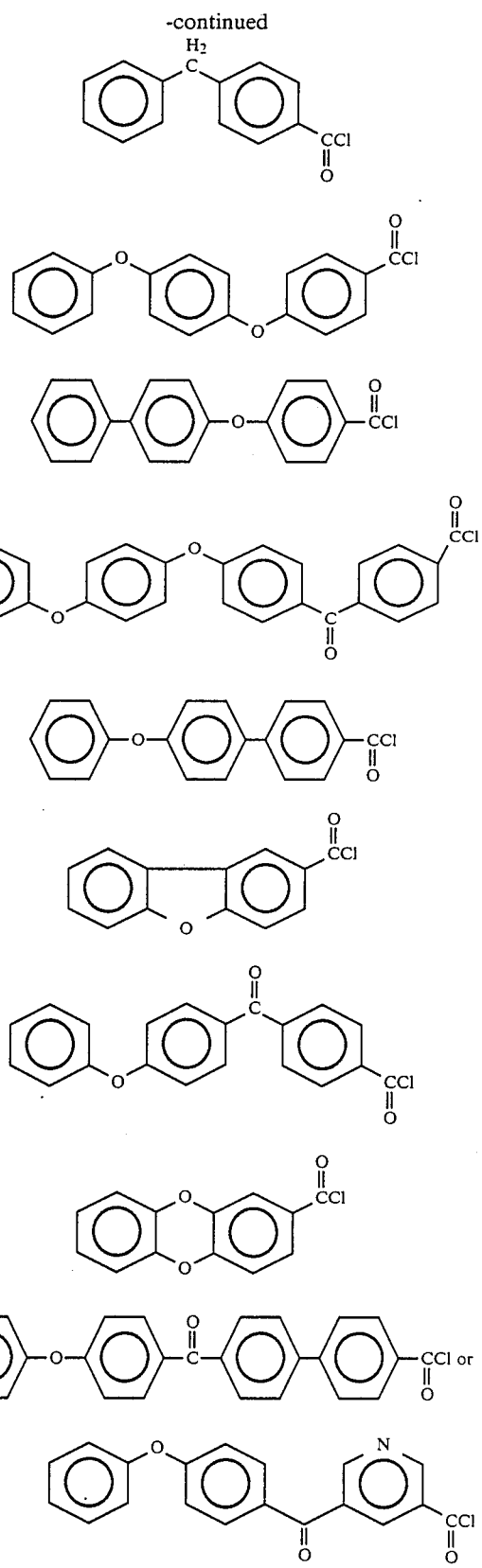

while the above examples are all carboxylic acid chlorides, it is to be understood that other acid derivatives containing a leaving group other than Cl can be employed. Further, sulfonic acid analogues of such compounds can be used for preparing the corresponding arylene sulfone oligomers.

Activated monomers of the formula

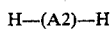

include, for example, compounds of the formula:

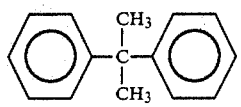

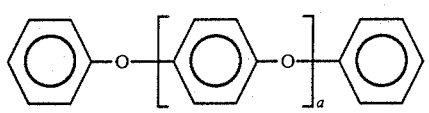

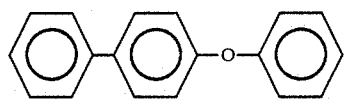

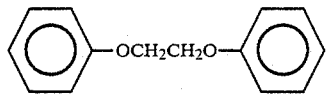

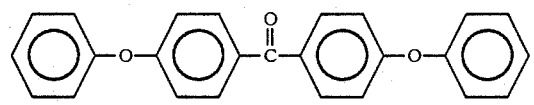

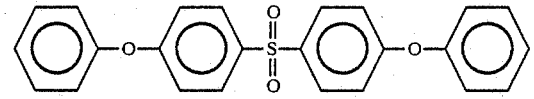

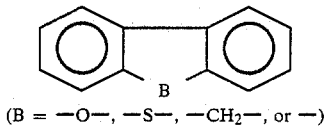

(B = —O—, —S—, —CH$_2$—, or —)

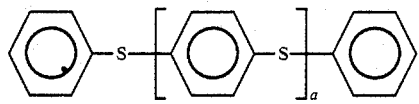

 or

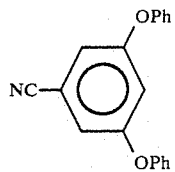

Monomers of the formula

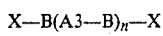

include dicarboxylic or disulfonic acid chlorides or other acid derivatives containing a suitable leaving group, for example, compounds of the following formulae and their sulfone analogues:

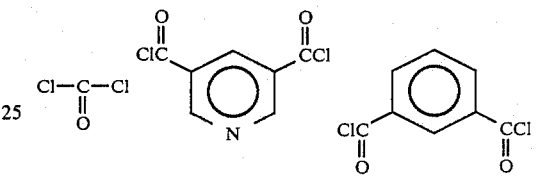

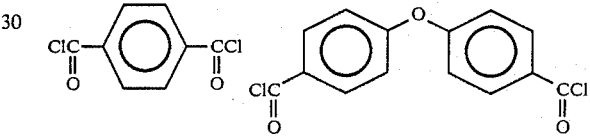

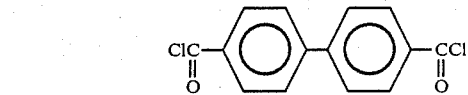

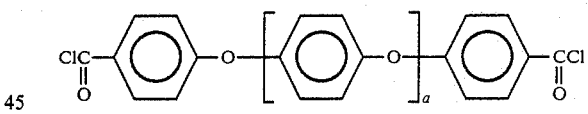

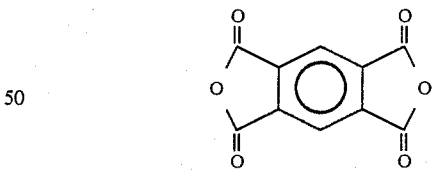

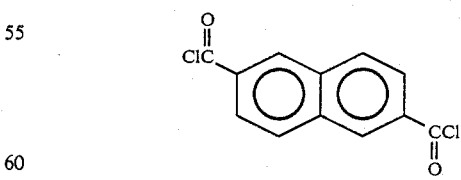

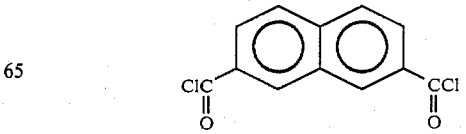

-continued

[Chemical structures showing:
- Diphenyl ketone with ClC(=O) groups at para positions
- Structure with central C=O connecting two aryl groups each bearing two C(=O)O groups
- Biphenyl-type structure with Z linker and ClC(=O) groups
- Dibenzofuran/thiophene/fluorene-type structure with B, B' bridges and two ClC(=O) groups
- Similar tricyclic structure with B, B' bridges and ClC(=O) groups]

(B,B' = —O—, —S—, —CH$_2$— or —)

wherein Z' is as defined above and a is 0, 1 or 2.

As with other electrophilic oligomerization reactions of this type, the monomer used should be relatively free of any impurities which would interfere with the reaction.

The process of the instant invention comprises the preparation of arylene ketone and arylene sulfone oligomers using a reaction medium comprising free Lewis acid and a complex between a Lewis acid and a Lewis base and optionally a diluent. The term "complex" is used to mean any product of the reaction between the Lewis acid and the Lewis base. A diluent is employed if the complex is a solid at reaction temperatures and can be present, if desired, when the complex is liquid. It is to be understood however that while the process of this invention has unique advantages for the preparation of all-para arylene ether ketones, the process of this invention can also be used to readily produce other arylene ketones including, for example, meta and mixed meta and para isomers and various co-oligomers having other functional groups in the polymer chain.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred.

The amount of Lewis acid used in the practice of this invention varies depending on the particular monomers and reaction medium selected. In all instances at least about one equivalent of Lewis acid per equivalent of carbonyl groups present in the monomer system is used plus an amount effective to act as a catalyst for the reaction (also referred to herein as a catalytic amount). Generally a catalytic amount added is from about 0.05 to about 0.3 equivalents of Lewis acid per equivalent of acid halide in the reaction mixture. Additional amounts of Lewis acid are also required depending on the nature of the monomers and the reaction conditions in a manner as set forth below. Further, if a comonomer containing other basic species, such as sulfone groups, is used, additional Lewis acid may be required.

In a preferred embodiment of the invention, the reaction is controlled by the addition of a controlling agent which, inter alia, suppresses undesirable side reactions, particularly alkylation and/or ortho substitution of activated aryl groups. Suppression of side reactions results in an oligomer that can be reacted further, for example, to produce a block copolymer that is thermally stable, that is it does not degrade or cross-link when subjected to elevated temperatures, e.g. temperatures above the melting point of the block copolymer, for a period of time. For a block copolymer of this type to be suitable for melt processing, it must be able to withstand the processing temperatures for the required processing time. Typically these conditions require that the block copolymer can withstand temperatures up to about 30° C. above the melting or softening point of the polymer for periods of at least 30 minutes, preferably at least 60 minutes and most preferably at least 90 minutes, without undesired gel formation or substantial change in inherent viscosity.

Preferred controlling agents for the reaction are Lewis bases. The term "Lewis base" is used herein to refer to a substance capable of donating an unshared electron pair to a Lewis acid. Thus, the Lewis base forms a complex with the Lewis acid used in the reaction medium. It has been found that Lewis bases which form a 1:1 complex having a heat of association at least about that of diphenyl ether with the Lewis acid are preferred. For example, where aluminum trichloride is the Lewis acid the Lewis base used should form a 1:1 complex having a heat of association of at least about 15 kcal/mole, preferably at least about 20 kcal/mole and most preferably at least about 30 kcal/mole. While the heats of association are for a 1:1 Lewis acid/Lewis base complex consisting solely of these two components, the actual complex formed in the reaction medium need not be a 1:1 complex. A discussion on heats of association for Lewis acid/Lewis base complex is found in J. Chem Soc. (A), 1971, pages 3132–3135 (D. E. H. Jones et al) The Lewis base used should not be an acylating, alkylating or arylating agent nor should it be acylatable under the reaction conditions.

Mixtures of two or more Lewis bases can be used if desired. The Lewis base used as a controlling agent in the practice of this invention is an additional component added to the reaction medium. This does not include basic species formed in situ during the reaction.

Typical Lewis bases which can be employed include, for example, amides, amines, esters, ethers, ketones, nitriles, nitro compounds, phosphines, phosphine oxides, phosphoramides, sulfides, sulfones, sulfonamides, sulfoxides and halide salts.

Examples of specific organic Lewis bases that can be used in the practice of this invention are acetone, benzophenone, cyclohexanone, methyl acetate, ethylene carbonate, N-methyl-formamide, acetamide, N,N-dimethylacetamide, N-methylpyrrolidone, urea, tetramethylurea, N-acetylmorpholine, dimethyl sulfoxide, N,N-dimethylformamide, diphenyl sulfone, N,N-dimethylmethane-sulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, 4-dimethylaminopyridine, and the like. In addition to covalent organic compounds, suitable Lewis bases include inorganic salts which can form complexes with Lewis acids, for example, chlories, such as trimethylammonium chloride, tetramethylammonium chloride, sodium chloride or lithium chloride, perchlorates, trifluoro-methanesulfonates and the like.

Preferred Lewis bases for the reaction medium of this invention are N-methylformamide, N,N-dimethyl-formamide, N,N-dimethylacetamide, 1-methyl-2-pyrrolidone, tetramethylene sulfone (also known as sulfolane), n-butyroni-trile, dimethyl sulfide, imidazole, acetone, benzophenone, trimethylamine, trimethylamine hydrochloride, tetramethyl-ammonium chloride, pyridine-N-oxide, 1-ethylpyridinium chloride, lithium chloride, lithium bromide, sodium chloride, sodium bromide, potassium chloride, potassium bromide and mixtures thereof.

The amount of Lewis base present should be from 0.01 to about 4 equivalents per equivalent of acid halide groups present in the monomer system. Amounts greater than 4 equivalents could be employed, if desired. However, no additional controlling effect is usually achieved by adding larger amounts. Thus, it is preferred to use no more than about 4 equivalents and generally about 2 equivalents. Preferably at least about 0.05, preferably at least about 0.1 and most preferably at least about 0.5 equivalents of Lewis base per equivalent of acid halide groups present should be used. The particular amount of Lewis base added depends to a certain extent on the nature of the monomers present.

The reaction temperature can be from about −50 C. to about +150 C. It is preferred to start the reaction at lower temperatures, for example at about −50 to about −10 C particularly if the monomer system contains highly reactive monomers. After reaction has commenced, the temperature can be raised if desired up to about 150° C. or even higher, for example, to increase the rate of reaction. It is generally preferred to carry out the reaction at temperatures in the range of between about −30 C. and +25 C (room temperature).

While it is not understood exactly how the Lewis base acts to control the reaction, it is believed that one or more of the following factors may be involved. The Lewis acid/Lewis base complex appears to influence the catalytic activity of Lewis acid, so as to substantially eliminate all ortho or meta acylation or sulfonylation. Moreover if a diluent such as methylene chloride or dichloroethane is used, the Lewis acid/Lewis base complex substantially reduces the tendency of the diluent to act as an alkylating agent by competing with the diluent for available Lewis acid and thereby suppressing alkylation of the oligomer. Alkylation of the oligomer in the para position caps the reaction while alkylation in the ortho position introduces undesired reactive sites in the oligomer chain which can lead to branching or cross-linking.

A non-protic diluent can also be employed, if desired. Advantageously, the diluent should dissolve the Lewis acid/Lewis base complex and the resulting oligomer/Lewis acid complex but this is not an essential requirement of the diluent. It should also be relatively inert toward Friedel-Crafts reactions.

The diluent is used in an amount from 0 to about 93% by weight, based on the weight of the total reaction mixture. As is known in reactions of this type, the reactions can be run neat, that is without the presence of a diluent. This is true for the process of this invention whether or not a Lewis base is used. As discussed in more detail below, it has been found that the monomer to diluent molar ratio can contribute to control of the reaction to yield the desired product.

Use of an alkylating or acylating diluent can lead to undesired side reactions as mentioned above. When such solvents are employed control of the reaction by techniques taught in this specification suppresses such alkylation or arylation. The result is a thermally stable, essentially linear oligomer.

The molecular weight of the oligomer, the degree of branching and amount of gelation is controlled by the use of, for example, capping agents as described in U.S. Pat. No. 4,247,682 to Dahl, the disclosure of which is incorporated herein by reference. The molecular weight of the oligomer can also be controlled by a reaction utilizing a two-monomer system as described above, by employing an excess of one of the monomers generally in an amount of at least 1.5 mol %, preferably at least 2.0 mol %.

Capping agents, when employed, are added to the reaction medium to cap the oligomer on at least one end of the chain. This terminates continued growth of that chain and controls the resulting molecular weight of the oligomer, as shown by the inherent viscosity of the oligomer. Judicious use of the capping agents results in an oligomer within a selected narrow molecular weight range, decreased gel formation during reaction, and decreased branching of the oligomer chains and increases melt stability. Both nucleophilic and electrophilic capping agents can be used to cap the oligomer at each end of the chain.

Preferred nucleophilic capping agents are 4-chlorobiphenyl, 4-benzenesulfonylphenyl phenyl ether, 4-phenoxybenzophenone, 4-(4-phenoxyphenoxy)benzophenone, 4,4'bisphenoxybenzophenone and the like generally in amounts of at least about 1.5 mol %, preferably at least about 2.0 mol %. The precise amount required varies both with the capping agent used and with the nature of the polymer thus capped.

Typical electrophilic capping agents are compounds of the formula

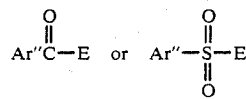

wherein Ar" is phenyl, 3-chlorophenyl, 4-chlorophenyl, 4-cyanophenyl, 4-methylphenyl or an aromatic group substituted with an electron withdrawing substituent and E is halogen or other leaving group. Preferred electrophilic capping agents include benzoyl chloride, benzenesulfonyl chloride and the like.

Functionalized capping agents which terminate at least one end of the oligomer chain are particularly useful in the practice of this invention. Suitable functionalized activated nucleophilic capping agents have the general formulae

HA4R wherein A4 is a divalent aromatic moiety and R is a Br, Cl or F atom or a hydroxy, alkoxy, alkene, alkyne, biphenylene, nitro, ester, acid, cyano, amino, mono- or di-substituted amino, amide, mono or di-substituted amide or an imide group. Suitable electrophilic capping agents have the formulae R(A4—D)$_m$—X wherein A4, is a divalent aromatic moiety, D is

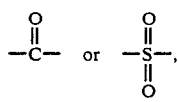

m is 1 or 2, X is halogen and R has been defined above.

In a two monomer system as described above termination with the functionalized group —B—X as defined can be obtained by employing an excess of the electrophilic monomer to control the molecular weight of the oligomer. In some circumstances it is advantageous to use an excess of the nucleophilic monomer.

Decomplexation can be accomplished by treating the reaction mixture with a decomplexing base after completion of polymerization. The base can be added to the reaction medium or the reaction medium can be added to the base. The decomplexing base must be at least as basic towards the Lewis acid as the basic groups on the polymer chain. Such decomplexation should be effected before isolation of the oligomer from the reaction mixture.

The amount of decomplexing base used should be in excess of the total amount of bound (complexed) and unbound Lewis acid present in the reaction mixture and is preferably twice the total amount of Lewis acid. Typical decomplexing bases which can be used include water, dilute aqueous hydrochloric acid, methanol, ethanol, acetone, N,N-dimethyl-formamide, N,N-dimethylacetamide, pyridine, dimethyl ether, diethyl ether, tetrahydrofuran, trimethylamine, trimethylamine hydrochloride, dimethyl sulfide, tetramethylenesulfone, benzophenone, tetramethylammonium chloride, isopropanol and the like. The decomplexed polymer can then be removed by conventional techniques such as adding a nonsolvent for the polymer which is a solvent for or miscible with the Lewis acid/Lewis base complex and the Lewis acid; spraying the reaction medium into a non-solvent for the polymer; separating the polymer by filtration; or evaporating the volatiles from the reaction medium and then washing with an appropriate solvent to remove any remaining base/catalyst complex and diluent from the polymer.

In the following examples inherent viscosities were determined in concentrated $H_2SO_4$ at 0.2% concentration.

EXAMPLE 1

This example illustrates the preparation of oligomeric poly(phenylene-ether-phenylene-ether-phenylene-carbonylphenylene-carbonyl). Aluminium chloride (2.933 g, 0.022 mol) was weighed into a 125 ml bottle and the bottle sealed with a silicone rubber stopper then 9 ml of dichloroethane (DCE) added at $-10°$ C. (this and all the other ingredients were added using a syringe). Dimethylformamide (DMF) was slowly added with shaking over approximately one minute. A mixture of 1,4-diphenoxybenzene (DPB: 1.312 g, 0.005 mol) and terephthaloyl chloride (TPC: 0.812 g, 0.004 mol) in 2 ml DCE was then added slowly with shaking over approx one minute. The syringe and monomer bottle were washed twice with 0.5 ml DCE. The polymerization mixture was shaken in a water bath at $-10$ C. overnight. The resultant deep orange viscous precipitate was worked up in methanol to give a white powder (yield 1.16 g, 63%; inherent viscosity, 0.17 dL/g). The C13 NMR was consistent with the expected structure.

EXAMPLE 2

This example illustrates the preparation of oligomeric poly(phenylene-ether-phenylene-ether-phenylene-carbonylphenylene-carbonyl). The procedure of Example 1 was followed using aluminium chloride (4.4 g, 0.033 mol) in DCE (9 ml), DMF (1.315 g, 0.018 mol), DPB (1.312 g, 0.005 mol) and TCE (1.218 g, 0.006 mol) in DCE (2 ml) and 2 washings with 1.25 ml aliquots DCE. The deep orange viscous precipitate was worked up in methanol to give the methyl ester of the oligomer as a white powder (yield, 1.48 g, 70%; inherent viscosity, 0.10 dL/g). The C13 NMR was consistent with the expected structure.

EXAMPLE 3

This example illustrates the preparation of oligomeric poly(phenylene-ether-phenylene-carbonyl). The procedure of example 1 was followed using aluminum chloride (4.000 g, 0.0275 mol) and lithium chloride (LiCl: 0.636 g, 0.015 mol) in 3 ml of DCE, 4-phenoxybenzoyl chloride (PBC: 2.326 g, 0.010 mol) and diphenylether (DPE: 0.085 g, 0.0005 mol) in 2 ml DCE and 2 washings with 0.5 ml aliquots DCE. The red orange viscous solution was worked up in methanol to give a white powder (yield, 1.50 g, 76%; inherent viscosity, 0.19 dL/g). The C13 NMR was consistent with the expected structure.

EXAMPLE 4

This example illustrates the preparation of oligomeric poly(phenylene-ether-phenylene-carbonyl). The procedure of example 1 was followed using aluminum chloride (4.000 g, 0.0275 mol) and lithium chloride (LiCl: 0.636 g, 0.015 mol) in 3 ml of DCE, 4-phenoxybenzoyl chloride (PBC: 2.326 g, 0.010 mol) and TPC (0.102 g, 0.0005 mol) in 2 ml DCE and 2 washings with 0.5 ml aliquots DCE. The red orange viscous solution was worked up in methanol to give the methyl ester of the oligomer as a white powder (yield, 1.46 g, 74%; inherent viscosity, 0.19 dL/g). The C13 NMR was consistent with the expected structure.

EXAMPLE 5

This example illustrates the preparation of oligomeric poly(phenylene-ether-phenylene-ether-phenylene-carbonylphenyl-ether-phenylene-carbonylphenylene-carbonyl). The procedure of Example 1 was followed using aluminum chloride (6.67 g, 0.005 mol) and DMF (1.425 g, 0.0195 mol) in 10 ml of DCE, DPB (1.832 g, 0.005 mol) as a solid and TPC (0.812 g, 0.004 mol) in 5 ml DCE and 2 washings with 3.0 ml aliquots DCE. The red orange viscous solution was worked up in methanol to give a white powder (yield, 2.06 g, 87%; inherent viscosity, 0.2 dL/g). The C13 NMR was consistent with the expected structure.

EXAMPLE 6

This example illustrates the preparation of oligomeric poly(phenylene-ether-phenylene-ether-phenylene-carbonylphenylene-ether-phenylene-carbonyl-phenylene-carbonyl). The procedure of Example 1 was followed using aluminum chloride (7.200 g, 0.054 mol) and DMF (1.864 g, 0.0255 mol) in 10 ml of DCE, DPB (1.832 g, 0.005 mol) as a solid and TPC (1.218 g, 0.006 mol) in 5 ml DCE and 2 washings with 3.0 ml aliquots DCE. The red orange viscous solution was worked up in methanol to give the methyl ester of the oligomer as a white powder (yield, 2.14 g, 82%; inherent viscosity, 0.37 dL/g). The C13 NMR was consistent with the expected structure.

What is claimed is:

1. A method for the preparation of an arylene ketone or an arylene sulfone oligomer which comprises reacting, in the presence of free Lewis acid and a complex between a Lewis acid and a Lewis base, a monomer system comprising at least one self reacting monomer of the formula wherein A1 is a divalent aromatic moiety, H is a hydrogen displaceable under Friedel-Crafts conditions, B is

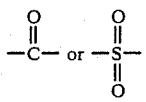

and X is a group displaceable under Friedel-Crafts conditions;
said reaction being conducted under such conditions as to produce an oligomer having an inherent viscosity of less than 0.6 and having at least 2 repeat units.

2. A method in accordance with claim 1 wherein said Lewis acid is selected from the group consisting of aluminum trichloride, boron trichloride, aluminum tribromide, antimony pentachloride, ferric chloride, gallium trichloride, and molybdenum pentachloride.

3. A method in accordance with claim 2 wherein said Lewis acid is aluminum trichloride.

4. A method in accordance with claim 2 wherein said Lewis acid is gallium trichloride.

5. A method in accordance with claim 1 wherein said Lewis base is selected from the group consisting of amides, amines, esters, ethers, thioethers, ketones, nitriles, nitro compounds, phosphines, phosphine oxides, phosphoramides, sulfides, sulfones, sulfonamides, sulfoxide and halide salts.

6. A method in accordance with claim 1 wherein said Lewis base is selected from the group consisting of acetone, benzophenone, cyclohexanone, methyl acetate, ethylene carbonate, N-methylformamide, acetamide, N,N-dimethylacetamide, N-methylpyrrolidone, urea, tetramethylurea, N-acetylmorpholine, dimethyl sulfoxide, diphenyl sulfone, N,N-dimethylmethanesulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, O-phenanthroline and 4-dimethyl aminopyridine.

7. A method in accordance with claim 1 wherein said Lewis base is selected from the group consisting of N-methylformamide, N,N-dimethylformamide, N,N-dimethylacetamide, 1-methyl-2-pyrrolidone, tetramethylene sulfone, n-butyronitrile, dimethylsulfide, imidazole, acetone, benzophenone, trimethylamine, trimethylamine hydrochloride, tetramethylammonium chloride, pyridine-N-oxide, 1-ethylpyridimium chloride, lithium chloride, lithium bromide, sodium chloride, sodium bromide and mixtures thereof.

8. A method in accordance with claim 1 wherein said Lewis acid is aluminum trichloride and said Lewis base is N,N-dimethylformamide, n-butyronitrile, tetramethylammonium chloride or lithium chloride.

9. A method in accordance with claim 8 wherein said Lewis base is N,N-dimethylformamide.

10. A method in accordance with claim 1 wherein said polymerization is carried out in the presence of a diluent.

11. A method in accordance with claim 10 wherein said diluent has a dielectric constant of at least about 2.5 at 24° C.

12. A method in accordance with claim 11 wherein said diluent has a dielectric constant in the range of from about 4.0 to about 25 at 24° C.

13. A method in accordance with claim 10 wherein said diluent is selected from the group consisting of for example, methylene chloride, carbon disulfide, o-dichlorobenzene, 1,2,4-trichlorobenzene, o-difluorobenzene, 1,2-dichloroethane, 1,2,3,4-tetrachloroethane and tetrachloroethylene.

14. A method in accordance with claim 1 wherein said monomer system comprises a self-reacting monomer of the formula

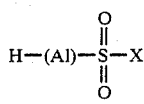

15. A method in accordance with claim 1 wherein said monomer system comprises a self-reacting monomer of the formula

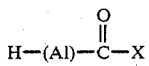

16. A method in accordance with claim 15 wherein said self-reacting monomer is selected from the group consisting of compounds of the formula

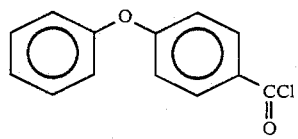

-continued

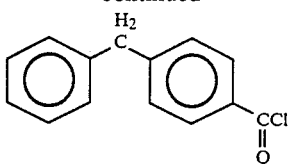
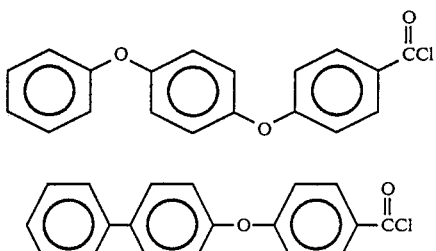
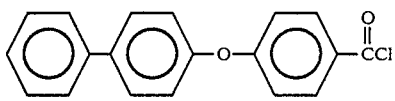
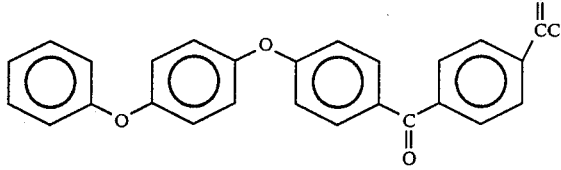
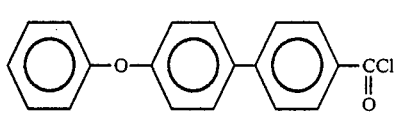
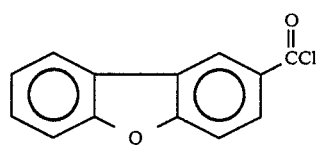
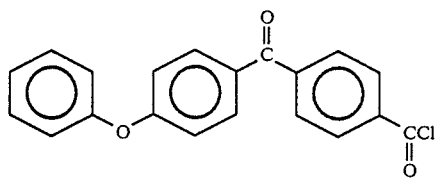
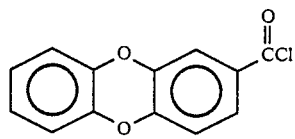
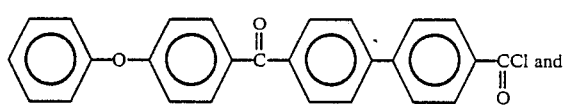
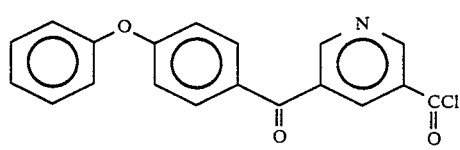

17. A method in accordance with claims 14 or 15 wherein A1 is an aromatic moiety of the formula

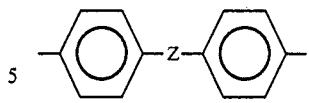

or

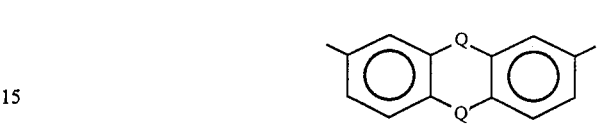

wherein Q' and Q" are independently selected from the group consisting or a direct linkage, —CH2—, —O— and —S—; and Z is a direct linkage, —O—, —S—, —O(CH2)$_n$O— and —CH2—

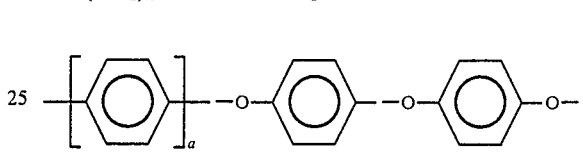

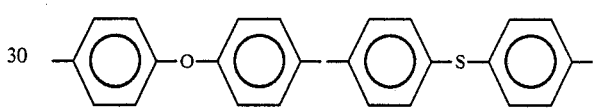

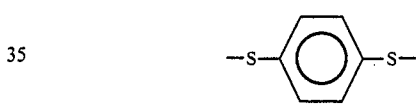

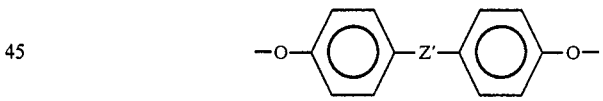

wherein a is 0–4 and Z' is $$-SO_2-\ -O-\ -S-\ -\overset{O}{\underset{\|}{C}}-\ -N=N-\ -(CF_2)_p-$$

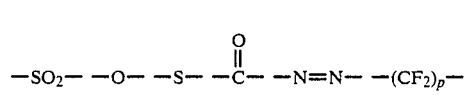

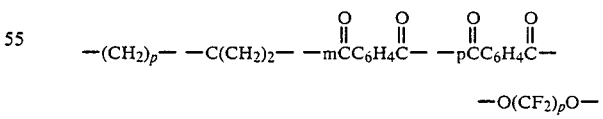

wherein p is 1–20.

18. A method in accordance with claim 15 wherein said self-reacting monomer is p-phenoxybenzoyl chloride.

19. A method in accordance with claim 15 wherein said self-reacting monomer is the N succinimido derivative of p-phenoxybenzoic acid.

20. A method in accordance with claim 1 wherein a capping agent is added to the reaction medium.

21. A method in accordance with claim 20 wherein said capping agent is a compound of the general formula

HA4R wherein A4 is a divalent aromatic moiety and R is a Br, Cl, or F atom or a hydroxy, alkoxy, alkene, alkyne, biphenylene, nitro, ester, acid, cyano, amino, mono- or di-substituted amino, amide, mono or di-substituted amide or an imide group.

22. A method in accordance with claim 20 wherein said capping agent is selected from the group consisting of 4-chlorobiphenyl, 4-phenoxybenzophenone, 4-(4-phenoxyphenoxy)benzophenone and 4-benzenesulfonylphenyl phenyl ether.

23. A method in accordance with claim 20 wherein said capping agent is selected from the group consisting of benzoyl chloride and benzenesulfonyl chloride.

* * * * *